United States Patent
Scholz (10) Patent No.: US 7,209,781 B2
(45) Date of Patent: Apr. 24, 2007

(54) METHOD FOR LOCALIZING AT LEAST ONE FOCAL LESION IN A BIOLOGICAL TISSUE SECTION

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 577 days.

(21) Appl. No.: 10/336,456

(22) Filed: Jan. 3, 2003

(65) Prior Publication Data

US 2003/0135131 A1 Jul. 17, 2003

(30) Foreign Application Priority Data

| Jan. 16, 2002 | (DE) | ................................ 102 01 472 |
| Jul. 8, 2002 | (DE) | ................................ 102 30 813 |
| Jul. 8, 2002 | (DE) | ................................ 102 30 815 |

(51) Int. Cl.
  *A61B 5/05* (2006.01)
(52) U.S. Cl. ................................ 600/547
(58) Field of Classification Search ............... 600/547, 600/407, 587, 372, 382
  See application file for complete search history.

(56) References Cited

U.S. PATENT DOCUMENTS 4,458,694 A * 7/1984 Sollish et al. ................ 600/547

FOREIGN PATENT DOCUMENTS

| WO | WO 96/12439 | * 5/1996 |
| WO | WO 99/48422 |   9/1999 |

OTHER PUBLICATIONS

Towards Virtual Electrical Breast Biopsy: Space-Frequency MUSIC for Trans-Admittance Data—Scholz IEEE Trans. on Medical Imaging, vol. 21, No. 6 Jun. 2002 pp. 588-595.

* cited by examiner

*Primary Examiner*—Max F. Hindenburg
*Assistant Examiner*—Fangemonique Smith
(74) *Attorney, Agent, or Firm*—Schiff Hardin LLP (57) ABSTRACT

In a method for localizing at least one focal lesion in a biological tissue section, the lesion exhibiting an electrical property different from the tissue section and the electrical property in the tissue section being essentially constant, a sequence of electrical excitation signals with different frequency is applied to the tissue section, electrical response signals at a number of measurement locations at a surface of the tissue section are measured that occur thereat due to the excitation signals, frequency-independent signal parts in the response signals are determined and further-processed input values of a localization step. Modeling of the tissue section and a determination of a set of lead fields are based on the input values. The lead fields transformed. The frequency-independent signal parts are compared to the transformed lead fields in the localization step, and the location of the transformed lead fields that best reproduce the frequency-independent signal parts is output as location of the lesion.

9 Claims, 6 Drawing Sheets

METHOD FOR LOCALIZING AT LEAST ONE FOCAL LESION IN A BIOLOGICAL TISSUE SECTION

BACKGROUND OF THE INVENTION

1. Field of the Invention

The present invention is directed to a method for localizing at least one focal lesion in a biological tissue section, the lesion exhibiting an electrical property different from the tissue section and whereby the electrical property in the tissue section being essentially constant.

2. Description of the Prior Art

A method for this purpose is disclosed in PCT Application WO 99/48422. In this method a sequence of electrical excitation signals with different frequency is applied to the tissue section, electrical response signals are measured at multiple measurement locations at a surface of the tissue section that occur thereat due to the excitation signals, frequency-independent signal parts in the response signals are determined and further-processed to produce input values for a localization step, and the tissue section is modeled and a set of lead fields is determined. For imaging by means of electrical impedance measurement, electrical currents are impressed and/or voltages applied to an examination subject (patient) at one or more locations. Voltages that arise due to the impressed currents are measured with M electrodes ($M \geq 1$) that are brought into electrical contact with the tissue section under examination at one or more locations. Currents that occur due to the applied voltages can be alternatively or additionally measured. The voltages and/or currents are defined for the subject (defined, for example, by a complex conductivity in the mathematical sense). Measured data thus are obtained at M different locations.

Spatial data (current values and/or voltage values) at different frequencies can be obtained by supplying at least one time-variable current and/or by applying at least one time-variable voltage. Frequency-dependent, measured spatial data are acquired in this way as a result of the frequency dependencies of the electrical conductivity that are typical for particular tissues. M×N data are obtained in the case of M measured data at N frequencies. As occurs, for example, given the TS2000 device of the TransScan Company, such data can be converted into time-independent susceptance values and capacitance values, i.e. into admittance values, and can be presented in conformity with the 2-dimensional electrode arrangement.

In a localization method of the type initially described an object of the invention is to increase the localization precision.

SUMMARY OF THE INVENTION

This object is achieved in a method of the type described above wherein the lead fields are transformed; by comparing the frequency-independent signal parts to the transformed lead fields in the localization step; and wherein the location of the transformed lead fields that best reproduce the frequency-independent signal parts is output as the location of the lesion. A model with significant properties adapted to the measured data is thus employed for the tissue section with the lesion. The localization precision thus is improved.

In an embodiment of the invention the lead fields are normalized in a first transformation. The magnitude of different lead field components thus are made dimensionless and independent of depth.

In another embodiment, the lead fields are transformed into orthogonal lead fields in a second transformation. The localization thus becomes more rugged and less susceptible to error, for example minimums are more pronounced. The lead fields required for the localization thus are also adapted better to the physical properties of the tissue section under examination and the lesion.

In an embodiment of the invention the orthogonal lead fields are determined from the lead fields by means of a singular value analysis. Methods for singular value resolution are widely employed. Their behavior given the most divergent input value combinations is well-known.

In a further embodiment of the invention electrical admittance data are determined from the response signals dependent on the location on the surface; by defining at least one maximum of the admittance data and the appertaining position or positions on the surface; and by determining at least one depth position of the corresponding lesion under the position of the corresponding maximum dependent on the position or the positions of the maximum or of the minimums. The outlay for localizing the lesion is thus considerably reduced.

In another embodiment of the invention the frequency-dependency of the biological signal source is determined from the response signals; and the lesion is classified dependent on the frequency dependency. The type of frequency dependency is defined by the type of tissue of the lesion.

DESCRIPTION OF THE PREFERRED EMBODIMENTS

Figure 1:
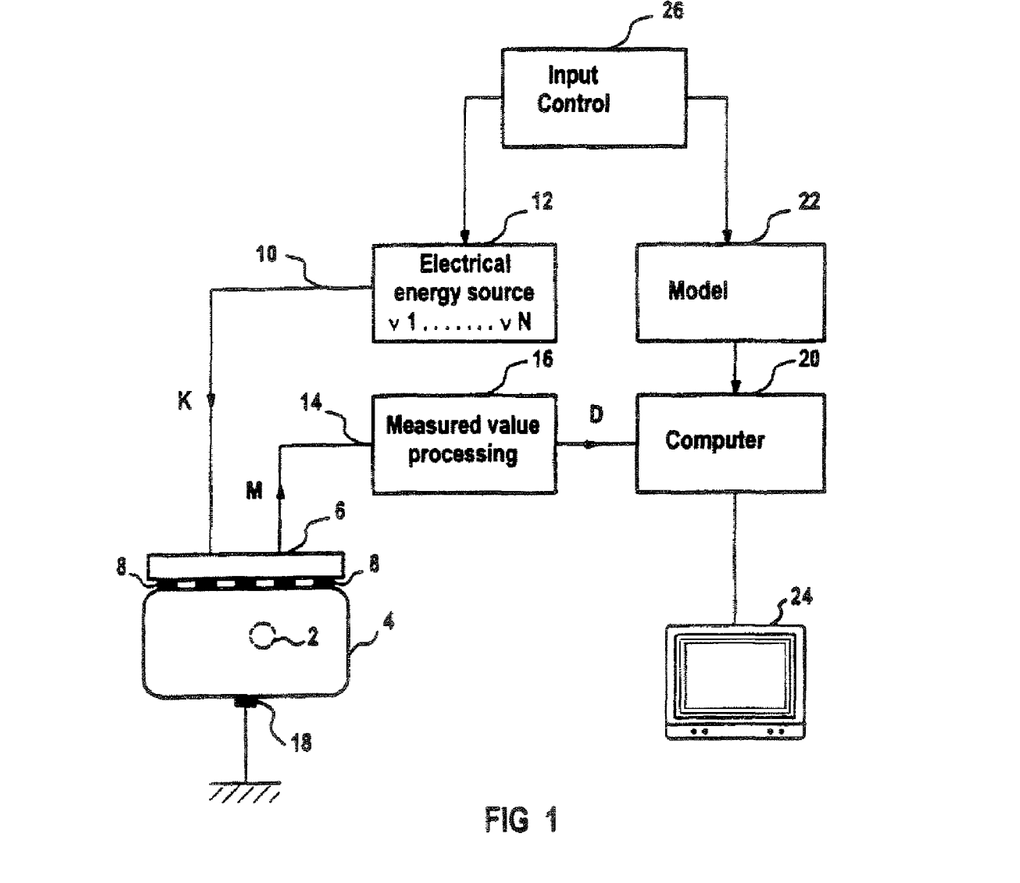
FIG. 1 is an overview showing the basic components of a device for localizing and classifying a focal lesion in a tissue section in accordance with the invention.

The overview in FIG. 1 shows a measurement and evaluation arrangement with which signal activities of a limited spatial region 2 in a biological tissue section 4 can be localized and identified. It is assumed that the spatial region 2 has an electrical conductivity that is different from that of the remaining tissue section, the remaining tissue section 4 exhibiting an essentially spatially constant electrical conductivity. These assumptions are adequately satisfied when the biological tissue section 4 is a female breast and the limited spatial region 2 is a tumor.

The measurement arrangement includes an applicator 6 having a number of electrodes 8 arranged in a spatially distributed manner that are brought into contact with the surface of the tissue section 4. For clarity, only five electrodes 8 are shown in FIG. 1. However, M=256 electrodes 8 should be arranged on an area of, for example, 9×9 $cm^2$ for an adequately exact localization.

The electrodes 8 are connected to an electrical energy source (current source or voltage source) 12 via electrical leads 10, and are connected as well, to a measured value processor 16 via electrical leads 14. A cooperating electrode 18 that is likewise connected to the power source 12 when potentials are measured, or to the voltage source 12 when currents are measured, and to the measured value processor 16 is arranged at that side of the tissue section 4 lying opposite the applicator. There is also the possibility of fashioning a part of the applicator 6 as a cooperating electrode.

With the electrical energy source 12, alternating currents, when measuring potentials, or alternating voltages, when measuring currents, are supplied to the biological tissue section 4 via K electrodes 8, with $1 \leq K \leq M$, in order to generate a spatial distribution of current thereat. Limited spatial regions 2 that have a different electrical conductivity than the surrounding tissue 4 are electrically polarized by the externally supplied currents or applied voltages so that the spatial regions 2 that are now polarized can be approximately considered as focal bioelectrical signal sources. The signal intensity is dependent on the magnitude and on the frequency-dependent, complex conductivity of the spatial region 2 under observation.

The localization and identification of spatially limited regions 2 is based on the locating and the determination of the strength of such bioelectrical signal sources by measuring the potentials generated by the supplied currents on the surface of the tissue section 4 at M electrode locations, or by measuring the currents generated in the tissue section 4 by the applied voltages at the M electrode locations. These measurements are supplied to an evaluation unit. Since the frequency dependency of the electrical conductivity in the limited spatial regions 3 represents an important quantity for the classification or identification of the corresponding tissue, currents from the current source 12, or voltages from the voltage source 12, can be generated with N different frequencies that lie in the range from 100 Hz through 500 kHz, for example, and can be supplied to the tissue section 4.

The measured value processor 16 includes, for example, meter amplifiers, filters and analog-to-digital converters. The measured value processor 16 is connected to one or more data inputs of an electronic computer 20. In addition to being supplied with the measured values, a model 22 of the tissue section 4 is made available to the computer. The aforementioned bioelectrical signal sources are localized and identified with the model 22, as described below. The result, for example, in the form of a graphic presentation of the anatomy of the tissue section wherein the location of the signal sources and thus of the spatial regions is marked, ensues via a monitor 24. Additionally, a quantity characterizing the signal activity that is dependent on the current or voltage frequencies is presented thereat. Since the model is determined by, among other things, the pattern of current that is generated in the tissue section 4 and by the feed location, a higher-ranking input and control 26 is provided. The number and the location of the feed electrodes 8 or of the voltage electrodes 8, the value of the current or voltage frequency and the model are prescribed therewith The localization method is explained with reference to FIG. 2 as an example. The input quantities thereof, i.e. the measured and the model data, shall be explained first, followed by the method steps.

Figure 2:
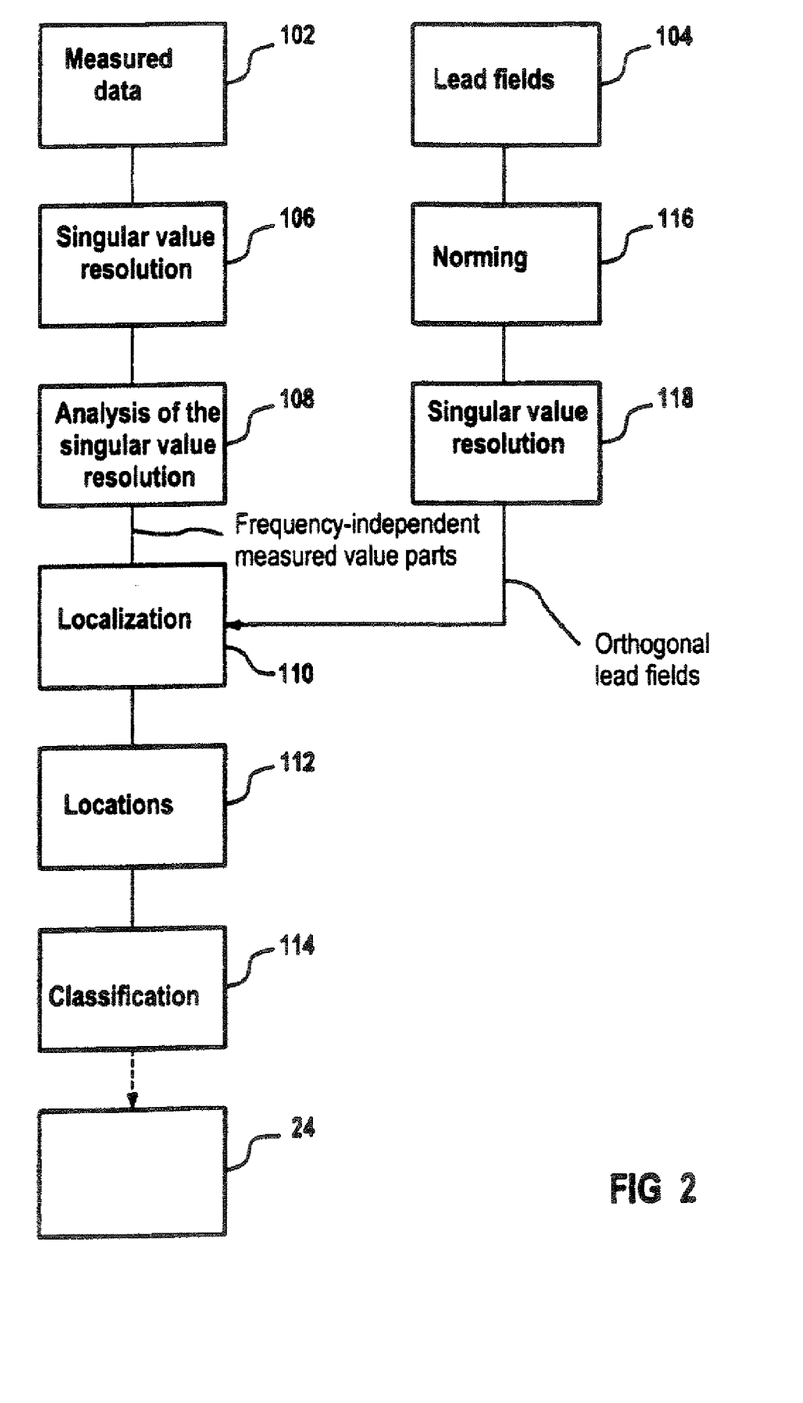
FIG. 2 illustrates the basic method steps for localizing a focal lesion in accordance with the invention.

The input quantities for the localization method are:

a) An M×N data matrix D with measured values (reference character 102) that is dependent on the M electrode locations $\vec{r}_m$, (m=1, ..., M) and the N current or voltage frequencies $v_n$, (n=1, ... N).

b) A set of K lead fields $L_k(\vec{r}_i, \vec{r}_m, \vec{n}_m)$, (k=1, ..., K), for example multi-pole lead fields that are provided with the reference character 104 in FIG. 2 and that are in turn dependent on a volume conductor model of the examination region 4,
a modeling of the conductivity inhomogeneities as biological signal sources at the location $\vec{r}_i$,
the type of measurement (measurement of potential and/or current), and
the measurement electrodes 8 in view of their position $\vec{r}_m$, their surface orientation, which is described by the normal vector $\vec{n}_m$, and their geometrical expanse.

The data D can be current and/or voltage values that were measured at a fixed time with respect to a reference signal, or can be linear combinations of current and/or voltage values that were measured at a number of times with respect to a reference signal. Due to coefficients that are used in the formation of the linear combinations, the data can be converted into susceptance and/or capacitance values. The following considerations are independent of the measurement time or times. The measurement times have therefore not been introduced into the equations as arguments. Measured data D are referred below occur, for example, on the basis of current data that were converted into admittance data. The admittance data can be exclusively real (only electrical conductance is present) or exclusively imaginary (only susceptance is present) or can be complex (both conductance as well as susceptance present).

The data matrix D can be derived from a linear combination of at least two datasets. For example, the difference between a dataset with lesion signals and a spatially neighboring dataset without lesion signal is observed. The magnitude of the exciting electrical fields is significantly reduced if not entirely eliminated in the difference data.

It may be necessary to supply post-processed measured data to the localization step. For example, edge artifacts can be eliminated by cutting off edge data. They can simulate a non-existent frequency dependency.

The simplest example of a volume conductor is conductive, infinite space. As used herein, "conductive" means that the conductivity of the medium being observed is complex. This means that both ohmic as well as dielectric properties are described. Another example of a volume conductor is the conductive, infinite half-space. Both models are independent of the patient.

The electrical lead fields for measurements of currents or measurements of potentials are the electrical field components or potentials generated by a point source having the intensity of one at the location that can be measured with the given measurement arrangement that is defined by the normal vector with respect to the $m^{th}$ measurement electrode at the location.

It is helpful for the further steps to combine the values of the $k^{th}$ lead field $L_k$ (k=1, ..., K) at the M measurement locations into an M-dimensional vector in the data space (symbolized by the underlining under L).

$$\underline{L}_k(\vec{r}) = (L_k(\vec{r}, \vec{r}_1), \ldots, L_k(\vec{r}, \vec{r}_M))^T \text{ with } k=1, \ldots, K \quad (1)$$

wherein $\vec{r}$ is the center of gravity location of the lesion.

The signal processing of the method is composed of 1. the singular value resolution of the data matrix D (reference character 106 in FIG. 2).
2. the analysis of the singular value resolution (reference character 108 in FIG. 2), and
3. the actual localization (reference character 110 in FIG. 2).

The singular value resolution 106 for the above, generally complex data matrix reads:

$$D = USV^H. \quad (2)$$

The following thereby apply:

U is a unitary M×M matrix that is only dependent on the indices of the electrode locations, S is the M×N singular value matrix with min(M,N) real singular values in the diagonal and, otherwise, disappearing elements, V is a unitary matrix N×N that is only dependent on the frequency indices, and H indicates the Hermitian conjugation.

The singular values are arranged according to their decreasing numerical size, i.e.

$$s_1 \geq s_2 \geq \ldots \geq s_{min(M,N)} \quad (3)$$

When the $q^{th}$ column vectors of the matrices U and V are referenced $\underline{u}_q, \underline{v}_q$, then the alternative tensor notation ( is the tensor product)

$$D = \sum_{q=1}^{min(M,N)} s_q \underline{u}_q \otimes \underline{v}_q^H \quad (4)$$

clearly shows that the $q^{th}$ singular value is exclusively linked to or: operated with the $q^{th}$ column vectors of U and V. The single and the double underlining at u and v indicate that they are M-dimensional and N-dimensional vectors, respectively.

The M indices of the column vectors $\underline{u}_q$ correspond to the consecutively numbered indices of the quadratically arranged measurement electrodes. Accordingly, these column vectors can be reshaped into $\sqrt{M} \times \sqrt{M}$-dimensional matrices, and the real/imaginary parts can be presented like two-dimensional measured value distributions. These column vectors are frequency-dependent, ortho-normed base vectors in the M-dimensional data space and are referred to herein as eigen-maps since they can in turn be presented as measured value distribution over the electrode arrangement. In the case of a 16×16 data matrix D, a $\underline{u}_q$ vector is 256-dimensional. Accordingly, it can be entered as a generally complex 16×16 measured value distribution.

The singular value analysis 108 yields the number $Q_{dom}$ of significant singular values, and thus the number of independent signal sources.

A spherical inhomogeneity in the otherwise homogeneous volume conductor, for example, generates a singular value spectrum with two significant singular values ($Q_{dom}=2$) when the two conductivity components (environment and sphere) exhibit different frequency behavior.

The appertaining column vectors $\underline{u}_q$ are considered base vectors of a (frequency-independent) $Q_{dom}$-dimensional signal space in the M-dimensional data space. The remaining M $Q_{dom}$ column vectors are then the base vectors of the orthogonal signal space. This space is referred to as noise space in earlier references.

Seeking focal conductivity inhomogeneities corresponds to the search for the locations/center of gravity locations of induced signal sources. This search by means of a computer requires the discrete representation of the assumed model volume conductor that the body region 4 to be examined should mathematically simulate.

Since lesions generate signal peaks in the two-dimensional measured value distributions dependent on depth, size and orientation, the search area can be limited to the region under the signal peak. A beneficial search is the search along a line in depth direction under a sharply pronounced peak.

The mathematics of the search strategy generate model data at every grid location with generally transformed lead fields and compare the data to the frequency-independent signal space obtained from the measured data. The locations at which a distance dimension between signal space and model data space assumes a local minimum are interpreted as locations of actual signal sources, and thus of the lesions 2.

The model data are derived from a transformation of the lead fields. An advantageous transformation includes initially normalizing the K lead fields L k (k=1, . . . , K) from (1) (processing step 116). The individual lead fields are respectively referenced to their norm, so that the normed lead fields $\underline{L}_k^{(n)}$ derive as follows:

$$\underline{L}_k^{(n)} = \frac{\underline{L}_k}{\|\underline{L}_k\|} \quad (5)$$

With, for example, a singular value resolution 118 of the M×K lead field matrix $L^{(n)}$, orthogonalized lead fields are then acquired, as represented below. The normalization is indicated by the index (n).

$$L^{(n)} = (\underline{L}_1^{(n)}, \ldots, \underline{L}_K^{(n)}) = U_L S_L V_L^T \quad (6)$$

For clarity, the arguments of the lead fields, the location vectors of the source location, were omitted. The first K column vectors $\underline{U}(\vec{r})_{L,k}$, (k=1, . . . , K) of the matrix UL are the sought, source location-dependent, ortho-normed lead fields.

For the localization 110, a check is carried out at each location $\vec{r}$ of the discretely represented volume conductor to see how great the distance is between the transformed lead fields $\underline{U}(\vec{r})_{L,k}$ and the signal space. The following function is a suitable dimension:

$$F_k(\vec{r}) = 1 - \sum_{i=1}^{Q_{dom}} (\underline{u}_i^H \cdot \underline{U}(\vec{r})_{L,k})^2. \quad (7)$$

This function corresponds to the projection value of the transformed lead field onto the orthogonal signal space because $$F_k(\vec{r}) = |P\underline{U}(\vec{r})_{L,k}|^2 \quad (8)$$

since $$P = 1 - \sum_{q=1}^{Q_{dom}} \underline{u}_q \otimes \underline{u}_q^H$$

represents the projection matrix onto the orthogonal signal space.

The starting equation for the derivation of 0 is $$\sum_{i=1}^{Q_{dom}} c_i \underline{u}_i = \underline{U}_{L,k} \quad k = 1, \ldots, K. \quad (9)$$

When the solution for the coefficient $c_i$ is inserted into the evaluation criterion $$F_k(\vec{r}) = \left| \sum_{i=1}^{Q_{dom}} c_i u_i - \underline{U}_{L,k} \right|^2 \qquad (10)$$

then the expression in 0 follows for.

The actual localization function F is the minimum value of the distances $F_k$. It is defined by $$F(\vec{r}) = \min_k \{F_k(\vec{r})\}. \qquad (11)$$

The local minimums of the localization function are ordered monotonously ascending according to their numerical values. The locations that are to be allocated to the first $Q_{dom}-1$ local minimums are viewed as locations of signal sources. The reduction by one takes into consideration that a significant singular value is caused by the tissue surrounding the signal source. In the evaluation, however, those local minimums that lie below the noise threshold are precluded as signal locations.

The reduction by one is omitted in the case of difference data that eliminate the amount of the electrical field excited from the outside.

For the classification 114, frequency-dependent electrical parameters that characterize the lesion and are complex in the mathematical sense are calculated from the admittance data of various frequencies at the located lesion locations. These parameters are a function of the conductivities of the lesion and of the surrounding tissue. These electrical parameters are multi-pole moments in the case of a description of the lesion by a multi-pole development with respect to the induced dipole distribution in the lesion volume. The classification is explained as an example below on the basis of the determination of electrical multi-pole moments.

The starting data for the classification or for the tissue determination are:

1. N admittance datasets $Y_n$ for the N voltage frequencies $f_n$, (n=1, . . . , N), and
2. a set of K multi-pole lead fields $L_k$, (k=1, . . . , K) that describe the creation of the measured values as a result of the $k^{th}$ multi-pole moment at a given location.

The admittance values $Y_n(\vec{r}_m)$, (m=1, . . . , M) measured at M locations given the frequency fn are combined into an M-dimensional data vector $\underline{Y}_n$.

$$\underline{Y}_n = (Y_n(r_1), \ldots , Y_n(r_M))^T, \qquad (12)$$

wherein $Y_n(\vec{r}_m) = G_n(\vec{r}_m) + i2\pi f_n C_n(\vec{r}_m)$. G and C are electrical conductance and capacitance that are allocated to the measurement location $\vec{r}_m$ at the frequency $f_n$.

The individual multi-pole lead fields $L_k(\vec{r}_m, \vec{n}_m, \vec{r})$,(k=1, . . . , K) are model measured values of the $k^{th}$ punctiform unit multi-pole at the location $\vec{r}$. They are dependent on
the volume conductor model,
on the type of measurement (measurement of potential and/or current: of current here),
on the measurement location and on the normal vector with respect to the measuring electrode, and
on the location of the punctiform multi-pole, which is interpreted as the center of gravity location of the localized lesion.

In the case of measuring currents, below is shown as an example of how the admittance data interrelates to the externally excited electrical background field and the induced multi-pole moments of the localized lesions. First, the admittance values measured at the location $\vec{r}_m$ are established by the current density $\vec{j}$, by the normal vector $\vec{n}_m$ onto the electrode surface at the measurement location, by the value of the electrode area $A_{electr}$ and by the amplitude $U_o$ of the applied alternating voltage:

$$Y_n(\vec{r}_m) = \vec{n}_m \cdot \vec{j}(\vec{r}_m, f_n) \cdot \frac{A_{electr}}{U_o} \qquad (13)$$

The index n and the quantity $f_n$ reference the $n^{th}$ measurement frequency.

In the example of the multi-pole model, the current density can be expressed by the electrical background field $\vec{E}_{bgrd}$, by the conductivity $k_{sur}$ at the measurement surface and the multi-pole moments $p_k(\vec{r}_l, f_n)$ of the $N_{loci}$ lesions localized at the locations $\vec{r}_l$,(l=1, . . . ,$N_{loci}$), said multi-pole moment being allocated to the k lead fields:

$$\vec{n}_m \cdot \vec{j}(\vec{r}_m, f_n) = \kappa_{sur}(f_n)\vec{n}_m \cdot \vec{E}_{bgrd}(\vec{r}_m, f_n) + \qquad (14)$$
$$\sum_{l=1}^{N_{lost}} \sum_{k=1}^{K} L_k(\vec{r}_m, \vec{n}_m, \vec{r}_l) p_k(\vec{r}_l, f_n).$$

Using vector and matrix notation, the above equation can be written in more compact form. Let the vector of the above-introduced normal components of the current densities—with f as frequency—be $$\underline{j}(f) = (j_1(f), \ldots , j_M(f))^T \text{ with } j_m(f) = \vec{n}_m \cdot \vec{j}(\vec{r}_m, f). \qquad (15)$$

The vector of the normal components of the electrical background field is defined in a corresponding way:

$$\underline{E}_{bgrd}(f) = (E_{bgrd,1}(f), \ldots , E_{bgrd,M}(f))^T. \qquad (16)$$

with $E_{bgrd,m}(f) \equiv \vec{n}_m \cdot \vec{E}_{bgrd}(\vec{r}_m, f)$

The multi-pole moments allocated to the location $\vec{r}_l$ are combined in a vector:

$$\underline{p}(\vec{r}_l, f) = (p_1(\vec{r}_l, f), \ldots , p_K(\vec{r}_l, f))^T \qquad (17)$$

The M×K matrix of the lead fields of the punctiform multi-poles at the location $\vec{r}_l$ is:

$$L(\vec{r}_l) = \begin{bmatrix} L_1(\vec{r}_1, \vec{r}_l) & \cdots & L_K(\vec{r}_1, \vec{r}_l) \\ \vdots & \ddots & \vdots \\ L_1(\vec{r}_M, \vec{r}_l) & \cdots & L_K(\vec{r}_M, \vec{r}_l) \end{bmatrix} \equiv [L_1(\vec{r}_l) \ \ldots \ L_k(\vec{r}_l)] \qquad (18)$$

The underlining in the second matrix denotes the combining of the individual lead fields into an M-dimensional column vector.

Equation (14) is then written $$\underline{j}(f_n) = \kappa_{sur}(f_n)\underline{E}_{bgrd}(f_n) + \sum_{l=1}^{N_{loci}} \underline{L}(\vec{r}_l)\vec{p}(\vec{r}_l, f_n) \quad (19)$$

In the next step, an overall multi-pole vector and an overall lead field matrix are defined. The overall lead field matrix $\Lambda$ contains the lead fields of all source locations and, accordingly, is an $M \times N_{loci} \cdot K$ matrix, expressed as $$\Lambda = [\underline{L}(\vec{r}_1)\underline{L}(\vec{r}_2)\ldots\underline{L}(\vec{r}_{N_{loci}})]. \quad (20)$$

It should be noted that the number of lead fields to be observed can vary from source location to source location. The individual matrices $\underline{L}(\vec{r}_l),(l=1,\ldots N_{loci})$ are then $M \times K_l$-dimensional and the overall matrix is $M \times (K_1 + K_2 + \ldots + K_{N_{loci}})$-dimensional. In the general case that has just been recited, the overall multi-pole vector is a $(K_1 + K_2 + \ldots + K_{N_{loci}})$-dimensional column vector:

$$\tilde{p}(f) = (\vec{p}(\vec{r}_1,f)^T, \ldots, \vec{p}(\vec{r}_{N_{loci}},f)^T)^T) \quad (21)$$

Equations (14) and (19) contain a current density $$j_{sur}(f_n) = \kappa_{sur}(f_n)E_{bgrd}(f_n)$$

that is generated by the electrical background field. It can be handled in two ways in the linear equation system to be solved.

Possibility 1

The background field $\underline{E}_{bgrd}$ at the measurement surface is known and the conductivity $k_{sur}$ is unknown. The following relationship is derived from equations (13) through (21) between admittance and the quantities to be identified, conductivity Ksur and multi-pole moments:

$$\underline{Y}_n = \frac{A_{electr}}{U_o}(\underline{E}_{bgrd}(f_n)\Lambda)\begin{pmatrix}\kappa_{sur}(f_n)\\\tilde{p}(f_n)\end{pmatrix} \equiv \Lambda_1 \tilde{p}_1(f_n) \quad (22)$$

The matrix $\Lambda 1$ is an $M \times S$ matrix, $S = N_{loci} \cdot K + 1$ or $S = K_1 + K_2 + \ldots + K_{N_{loci}} + 1$. The vector $\tilde{p}_1$ is S-dimensional.

Possibility 2

The background field $\underline{E}_{bgrd}$ and the conductivity $k_{sur}$ are unknown. When it can be assumed that the background field under the measurement surface is constant, then the additional unknown is a background current density that is independent of measuring location. With $$\underline{E}_{bgrd} = E_{bgrd}1_{M\times 1} \text{ and } j_{sur}(f_n) = \kappa(f_n)E_{bgrd}(f_n), \quad (23)$$

wherein $1M\times 1$ is a one-dimensional column vector, then $$\underline{Y}_n = \frac{A_{electr}}{U_o}(1_{M\times 1}\,\Lambda)\begin{pmatrix}j_{sur}(f_n)\\\tilde{p}(f_n)\end{pmatrix} \equiv \Lambda_2\,\tilde{p}_2(f_n) \quad (24)$$

The matrix and vector dimensions of $\Lambda_2$ and $\tilde{p}_2$ are $M \times S$ and S, so $S = N_{loci} \cdot K + 1$ or $S = K_1 + K_2 + \ldots + K_{N_{loci}} + 1$ applies.

Possibility 3

The background field $\underline{E}_{bgrd}$ and the conductivity $k_{sur}$ are unknown. It is likewise assumed that the background current density is dependent on measuring location.

$$\underline{Y}_n = \frac{A_{Electr}}{U_o}(1_{M\times M}\,\Lambda)\begin{pmatrix}j_{sur}(f_n)\\\tilde{p}(f_n)\end{pmatrix} \equiv \Lambda_3\,\tilde{p}_3(f_n), \quad (25)$$

wherein $1_{M\times M}$ is a unit matrix $M \times M$. The matrix and vector dimensions are $M \times S$ and S, so $S = N_{loci} \cdot K + M$ or $S = K_1 + K_2 + \ldots + K_{N_{loci}} + M$ applies.

The linear equation systems (22), (24) and (25) are under-defined when M>S applies and are over-defined when M<S applies. The solution is established by the generalized inversion of the matrices $\Lambda_i$, (i=1,2,3).

The solution for the frequency $f_n$ (n=1, ..., N) reads $$\tilde{p}_i(f_n) = \Lambda_i^+ \underline{Y}_n, \ i = 1,2,3, \quad (26)$$

wherein $\Lambda_i^+$ represents the generalized inverse matrix.

The solution vectors $\tilde{p}_i$ (see Equation (22), (24) and (25)) for the various frequencies contains the sought frequency behavior of the multi-pole moments $\tilde{p}(f_n),(n=1, \ldots, N)$ at the previously localized center of gravity locations of focal lesions. As mentioned above, the multi-pole moments are mathematically complex quantities.

Figure 3A:
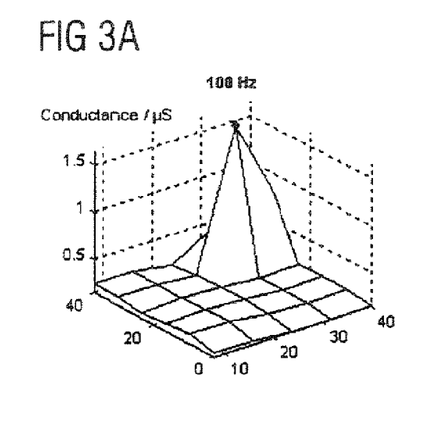
FIGS. 3A through 3D show the location-dependency of clinical guideline values of a malignant, focal breast lesion.
Figure 3B:
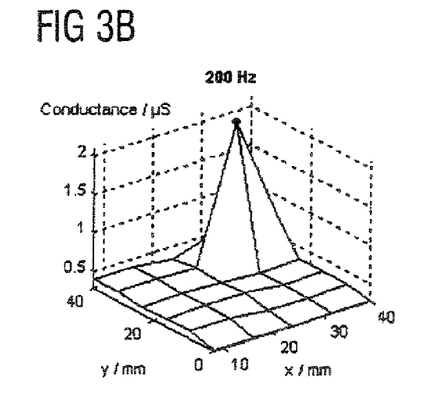
Figure 3C:
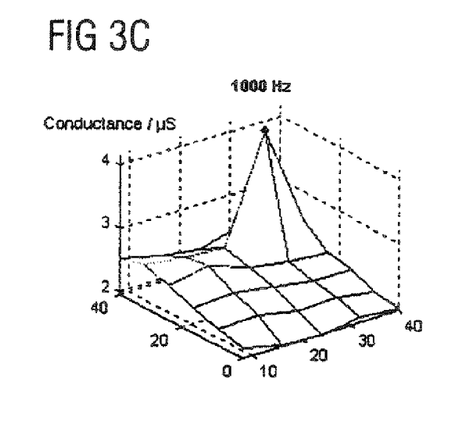
Figure 3D:
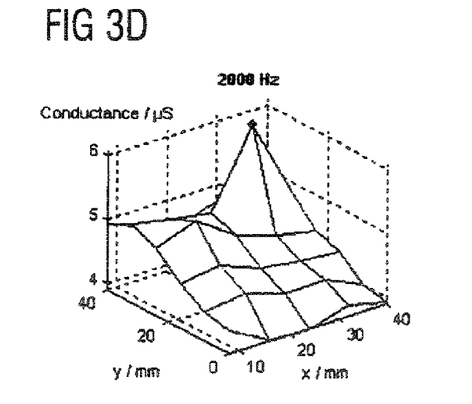
Figure 4A:
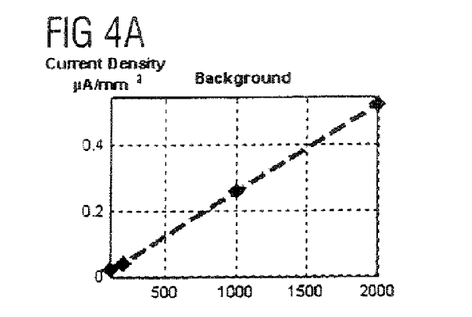
FIGS. 4A through 4F show the frequency behavior of the real part of multi-pole moments of the lesion.
Figure 4B:
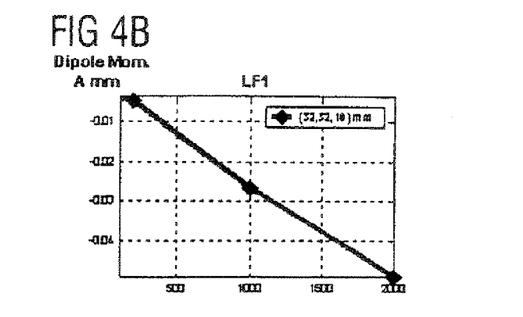
Figure 4C:
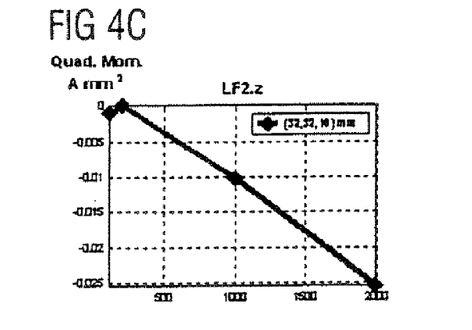
Figure 4D:
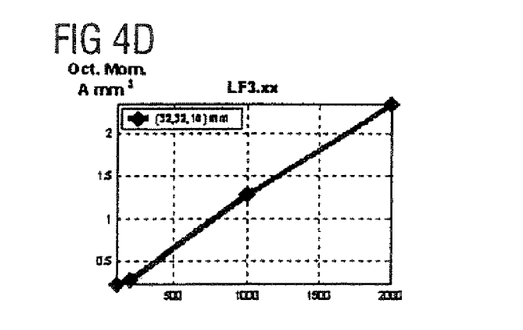
Figure 4E:
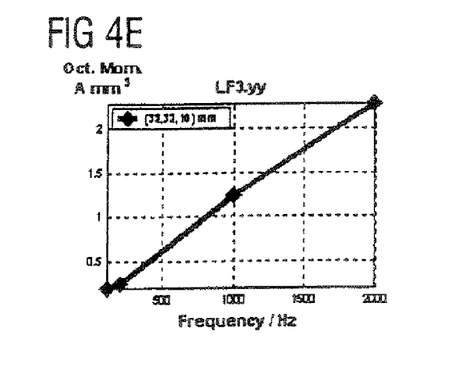
Figure 4F:
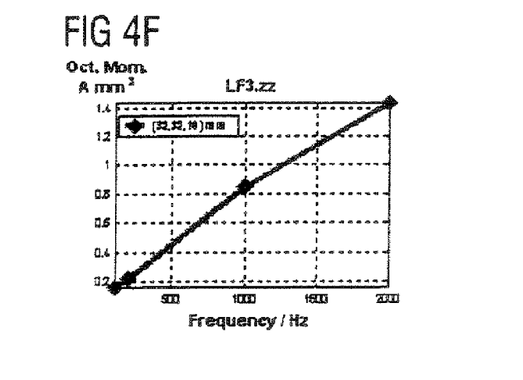

FIGS. 3A through 3D show clinical guideline value data of a malignant, focal breast lesion with reference to the surface of the applicator. FIG. 3A provides the guideline data at a frequency of 100 Hz, FIG. 3B at a frequency of 200 Hz, FIG. 3C at a frequency of 1000 Hz and FIG. 3D at a frequency of 2000 Hz. FIGS. 4A through 4F contain a graphic illustration of the multi-pole frequency behavior appertaining thereto. However, only guideline data were employed in this example, so that only the real parts of the effective multi-pole moments were calculated. Over the frequency, FIGS. 4A through 4F show the curve of the current density (FIG. 4A), the dipole moment (FIG. 4B), a quadrupole moment (FIG. 4C) and the octopole moments (FIGS. 4D through 4F). Only those components whose contributions lie above the noise level are shown. The measurement frequencies were 100, 200, 1000 and 2000 Hz.

The measured data contribution of the electrical background field can be reduced or even entirely eliminated when differences between datasets with and without lesion signals are taken into consideration. The dataset without lesion signals should thereby be registered in the immediate proximity of the surface where lesion signals were found.

After forming the difference of the data sets with and without lesion signal/signals, the following equation, which is to be inverted, then derives for the difference data $\underline{Y}_{diff,n}$ of the frequencies $f_n$, (n=1, ..., N):

$$\underline{Y}_{diff,n} = \Lambda\tilde{p}(f_n) \quad (27)$$

The contribution of the background is thereby considered eliminated. The matrix $\Lambda$ and the multi-pole moment vector $\tilde{p}$ have been defined above, see Equations (20) and (21).

Then, the multi-pole moments are:

$$\tilde{p}(f_n) = \Lambda^+ \underline{Y}_{diff}(f_n), \quad (28)$$

wherein $\Lambda^+$ is the generalized inverse matrix of $\Lambda$.

Figure 5:
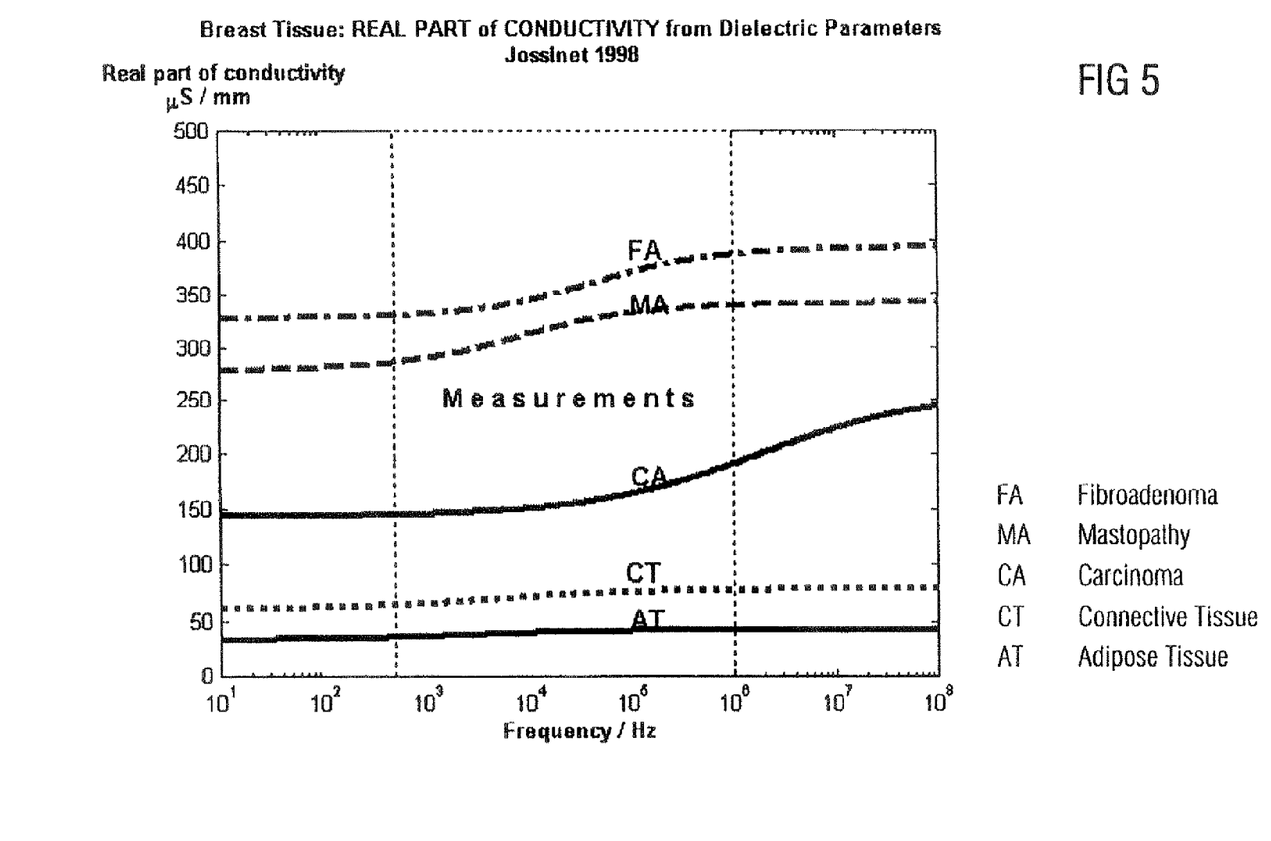
FIG. 5 is an illustration of the frequency-dependent real part of the conductivity of various tissue types.
Figure 6:
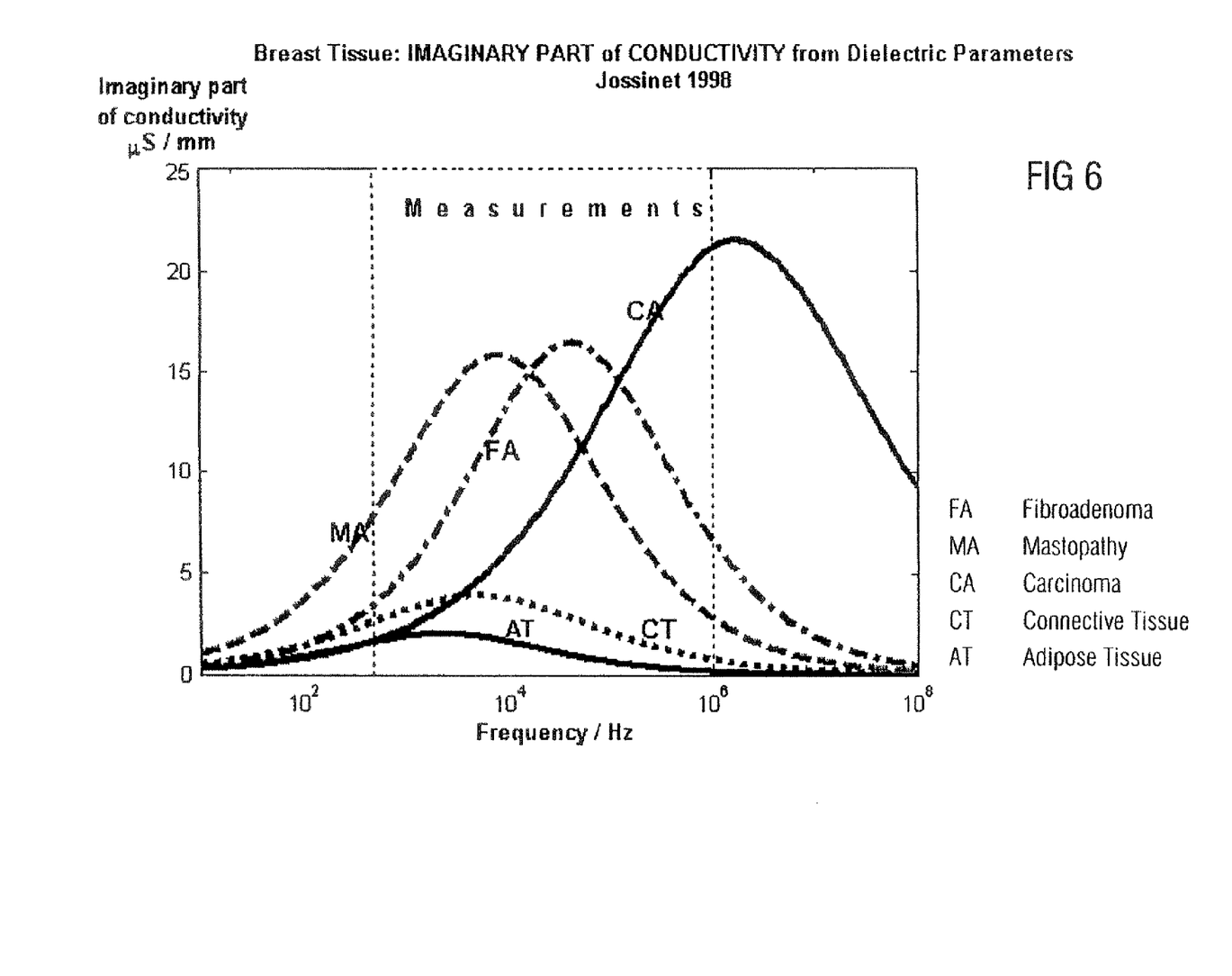
FIG. 6 is an illustration of the frequency-dependent imaginary part of the conductivity of various tissue types.

For various tissue types, FIG. 5 shows the real part of the conductivity and FIG. 6 shows the appertaining imaginary part dependent on the frequency. These values are known from the literature. For classification, the frequency-dependent values calculated from the measured values are compared to the known values.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for localizing at least one lesion in a biological tissue section, said lesion exhibiting an electrical property different from said tissue section, and said electrical property in said tissue section being substantially constant, comprising the steps of:

applying a sequence of electrical excitation signals with respectively different frequencies to said tissue section;

measuring electrical response signals, arising due to said excitation signals, at a plurality of measurement locations at a surface of said tissue section;

determining frequency-independent signal parts in said response signals and further-processing said frequency-independent signal parts to produce input values for a localization procedure; and in said localization procedure, modeling said tissue section dependent on said input values to produce a tissue section model and from said tissue section model determining a set of lead fields, and transforming said lead fields to obtain transformed lead fields, and comparing said frequency-independent signal parts to said transformed lead fields to identify a location of said transformed lead fields that best reproduces said frequency-independent signal parts, and providing said location as an output as the location of said lesion.

2. A method as claimed in claim 1 comprising transforming said lead fields by normalizing said lead fields in a first transformation, thereby obtaining normalized lead fields.

3. A method as claimed in claim 2 comprising transforming said lead fields by transforming said normalized lead fields, in a second transformation, into orthogonal lead fields.

4. A method as claimed in claim 3 comprising determining said orthogonal lead fields from said transformed lead field by a singular value resolution.

5. A method as claimed in claim 1 comprising modeling said tissue section as an electrical volume conductor.

6. A method as claimed in claim 1 comprising determining electrical admittance data from said response signals dependent on a location at said surface of said tissue section at which at least one maximum of said electrical admittance data occurs, and identifying at least one depth position in said tissue section of said lesion beneath said position on said surface of said maximum, dependent on at least one position of a peak selected from the group consisting of maximum peaks and minimum peaks.

7. A method as claimed in claim 1 comprising determining a frequency-dependency of a bioelectrical signal source from said response signals and classifying said lesion dependent on said frequency-dependency.

8. A method as claimed in claim 7 comprising representing said bioelectrical signal source by a multi-pole development.

9. A method as claimed in claim 1 comprising generating a matrix containing said response signals, and determining said frequency-independent signal parts in said response signals by singular value resolution of said matrix.

* * * * *